United States Patent [19]

Klayman et al.

[11] Patent Number: 4,493,930
[45] Date of Patent: Jan. 15, 1985

[54] MEDICINAL 2-ACETYL- AND 2-PROPIONYLPYRIDINE THIOSEMICARBAZONES AND PREPARATION THEREOF

[75] Inventors: Daniel L. Klayman, Chevy Chase; John P. Scovill, Rockville; Joseph F. Bartosevich; Carl J. Mason, both of Silver Spring, all of Md.; T. Scott Griffin, Orange, Calif.

[73] Assignee: The United States of America as represented by the Secretary of the Army, Washington, D.C.

[21] Appl. No.: 311,371

[22] Filed: Oct. 14, 1981

Related U.S. Application Data

[63] Continuation of Ser. No. 4,247, Jan. 4, 1979, Pat. No. 4,317,776.

[51] Int. Cl.$^3$ ................. C07D 401/12; A61K 31/495
[52] U.S. Cl. ................................. 544/360; 260/244.4
[58] Field of Search ............................ 544/360, 364; 260/244.4

[56] References Cited

U.S. PATENT DOCUMENTS

| | | | |
|---|---|---|---|
| 2,719,161 | 9/1955 | Behnisch et al. | 424/263 |
| 2,723,270 | 11/1955 | Scudi | 424/263 |
| 4,317,776 | 3/1982 | Klayman et al. | 544/360 |

FOREIGN PATENT DOCUMENTS 1084700  9/1967  United Kingdom ................ 424/263

OTHER PUBLICATIONS

Collins, F. M., et al., J. General Microbiology, (1982), 128, 1349–1356.
Dobek et al., Antimicrobial Agents and Chemotherapy, vol. 18, (1), 27–36 (1980).

Primary Examiner—Donald G. Daus
Assistant Examiner—S. A. Gibson
Attorney, Agent, or Firm—William G. Gapcynski; Werten F. W. Bellamy; Sherman D. Winters

[57] ABSTRACT

This invention relates to various 2-acetyl- and 2-propionylpyridine thiosemicarbazones which are substituted on the 4-nitrogen atom. These compounds are useful in the treatment of gonorrhea and, in addition, many are useful either in the treatment of malaria or bacterial infection. Also disclosed are several synthetic procedures used to prepare the thiosemicarbazones.

11 Claims, No Drawings

MEDICINAL 2-ACETYL- AND 2-PROPIONYLPYRIDINE THIOSEMICARBAZONES AND PREPARATION THEREOF

This is a continuation of application Ser. No. 4,247, filed Jan. 4, 1979, now U.S. Pat. No. 4,317,776.

DETAILED DESCRIPTION OF THE INVENTION

This invention relates to the use of the following compounds and their pharmaceutically-acceptable acid addition salts in the treatment of gonorrhea, malaria, or bacterial infection:

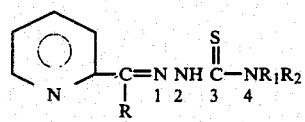

where R is methyl or ethyl;

$R_1$ is alkyl, preferably having 1 to 12 carbon atoms or, more preferably, 6 to 12 carbon atoms; cycloalkyl, preferably having 3 to 10 carbon atoms, substituted alkyl wherein the alkyl group preferably has 1 to 12 carbon atoms and the substituent group in amino, alkylamino (preferably 1 to 4 carbon atoms), dialkylamino (preferably 1 to 4 carbon atoms in each alkyl group), cycloalkyl (preferably 3 to 10 carbon atoms), COO alkyl (preferably 1 to 4 carbon atoms) in the alkyl group), phenyl, or pyridyl; alkenyl, preferably having 2 to 6 carbon atoms; alkynyl, preferably having 3 to 6 carbon atoms, substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl; napthyl; substituted phenyl or substituted naphthyl wherein the ring is mono-, di-, or trisubstituted and the substituents are alkyl (preferably 1 to 4 carbon atoms), halo (preferably fluoro), alkoxy (preferably 1 to 4 carbon atoms), hydroxy, pheroxy, trifluoromethyl, dialkyl (preferably dimethyl) amino, dialkylaminoalkyl (preferably diethylaminomethyl), or COO alkyl (preferably 1 to 4 carbon atoms in the alkyl group); pyridyl thienyl; indolyl; furyl; acridyl; quinolyl; or pyridazinyl and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:

(1) alkylenimino;
(2) alkylenimino which may contain one double bond and/or is mono- or disubstituted with alkyl (preferably 1 to 4 carbon atoms), hydroxy, phenyl, or benzyl;
(3) alkylenimino which is either bridged by an alkylene group (preferably 2 carbon atoms) or is fused to a phenyl ring; or is attached by a spiro linkage to an ethylene ketal group;
(4) homopiperazinyl; homopiperazinyl substituted with alkyl (preferably 1 to 4 carbon atoms); piperazinyl; or piperazinyl substituted with alkyl (preferably 1 to 4 carbon atoms), dialkyl (preferably 1 to 4 carbon atoms in each alkyl group), phenyl, COO alkyl (preferably 1 to 4 carbon atoms in the alkyl group), tri-fluoromethyl-phenyl, halophenyl, benzyl, or pyridyl; and
(5) morpholino, dialkyl (preferably 1 to 4 carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2, 5-dimethyl pyrrolidino; piperidino;

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2, 6-dimethyl piperidino; 3, 5-dimethyl piperidino; morpholino; 3, 5-dimethylmorpholino;

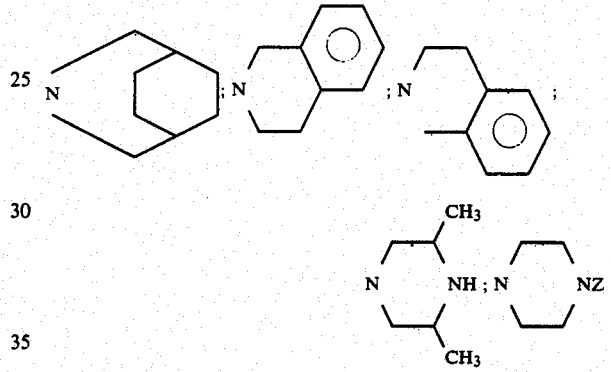

(wherein z is methyl, phenyl, 3-trifluoromethyl phenyl, benzyl, COO Et, 3-pyridyl, 2-pyridyl, or 4-fluorophenyl);

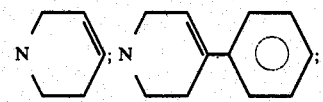

azacyclotridecyl;

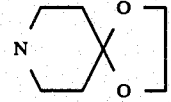

; or

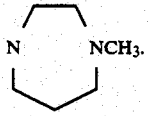

In this disclosure, it is understood that COO alkyl represents the alkyl carboxylic acid ester; for example, COO Et represents the ethyl carboxylic acid ester.

While evidence indicates that all of the above-described compounds and their pharmaceutically-acceptable acid addition salts are useful in the treatment of gonorrhea, in addition many of the compounds and salts are useful either in the treatment of malaria or bacterial infection. Such use of the above-described compounds and salts is included in the present invention. Moreover, the above-described compounds per se, and their pharmaceutically-acceptable acid addition salts, are included in the invention provided that: when $R_2$ is hydrogen, then $R_1$ cannot be ethyl, isopropyl, or monochlorophenyl.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts are mentioned hydrochloric and hydrobromic acids.

SYNTHETIC PROCEDURES

Three synthetic procedures proved to be useful for preparing the thiosemicarbazones of this invention.

In Scheme A, a primary amine was converted to the corresponding isothiocyanate (1), ordinarily by employing thiophosgene. Reaction of 1 with hydrazine afforded a thiosemicarbazide 2. Condensation of this intermediate with 2-acetylpyridine provided the 4-monosubstituted thiosemicarbazone 3. However, only thiosemicarbazones monosubstituted at position 4 can be prepared in this manner, Scheme A $$R_1NH_2 + C(=S)CL_2 \longrightarrow R_1-N=C=S \xrightarrow{H_2NNH_2}$$
$$1$$

$$R_1-NHC(=S)NHNH_2 \xrightarrow{2-Pyr(CH_3)C=O}$$
$$2$$

$$2-Pyr(CH_3)C=NNHC(=S)NHR_1$$
$$3$$

as 2-acetylpyridine proved to be usually resistant to condensation with 2, 4-disubstituted thiosemicarbazides.

In Scheme B, reaction of hydrazine and carbon disulfide in the presence of sodium hydroxide yielded a carbodithioate. Alkylation of this carbodithioate with either iodomethane or dimethyl sulfate gave methyl hydrazinecarbodithioate (4). Condensation of 4 with 2-acetylpyridine gave the versatile intermediate, methyl 3-[1-(2-pyridyl)ethylidene] hydrazinecarbodithioate, 5. Reaction of 5 with primary amines gave 4-monosubstituted thiosemicarbazones such as 3 while secondary amines or cyclic amines produced 4,4-disubstituted thiosemicarbazones, 6. In addition, reaction of 5 was not limited to more active nucleophiles, as excellent yields could be obtained with many primary aromatic amines. However, 5 was resistant to reaction with some secondary aromatic amines, such as N-methylaniline.

Scheme B $$H_2NNHC(=S)SCH_3 + 2-Pyr(CH_3)C=O \longrightarrow$$
$$4$$

$$2-Pyr(CH_3)C=NNHC(=S)SCH_3 \xrightarrow{HNR_1R_2}$$
$$5$$

-continued
Scheme B $$2-Pyr(CH_3)C=NNHC(=S)NR_1R_2$$
$$3, 6$$

Scheme C involved the reaction of 2-acetylpyridine with hydrazine to yield the hydrazone 7. Reaction of this hydrazone with an isothiocyanate 1 produced a 4-monosubstituted thiosemicarbazone 3. This reaction was especially useful when the required isothiocyanate was commercially available.

Scheme C $$2-Pyr(CH_3)C=O + H_2NNH_2 \longrightarrow 2-Pyr(CH_3)C=NNH_2 \xrightarrow{1} 3$$
$$7$$

WORKING EXAMPLES

The working examples set forth below illustrate the preparation of representative compounds and salts, but in no way limit the scope of the invention.

EXAMPLE 1

2-Acetylpyridine 4-allyl-3-thiosemicarbazone (Procedure C)

A solution of 2.7 g (0.02 mol) of 2-acetylpyridine hydrazone in 5 ml of MeOH was treated with 3.1 g (0.03 mol) of allyl isothiocyanate and the solution was heated at reflux for 3 hr. The solution was cooled and the product which formed was collected. The crude material was recrystallized 3 times from MeOH, affording 2.5 g (49%) of white needles of 2- cetylpyridine 4-allyl-3-thiosemicarbazone, mp 107° C.

Analysis Calcd. for $C_{11}H_{14}N_4S$: C, 56.38; H 6.02; N, 23.91; S, 13.68. Found: C, 56.09; H, 6.11; N, 24.36; S, 13.89.

EXAMPLE 2

2-Acetylpyridine 4-cyclohexyl-3-thiosemicarbazone (Procedure C)

A solution of 6.76 g (0.05 mol) of 2-acetylpyridine hydrazone in 10 ml of MeOH was treated with 7.2 g (0.05 mol) of cyclohexyl isothiocyanate and the solution was heated at reflux for 3 hr. The solution was chilled, and the crystals which formed were collected. Recrystallization of the product from 150 mL of MeOH afforded 6.40 g (46%) of white needles of 2-acetylpyridine 4-cyclohexyl-3-thiosemicarbazone, mp 155° C.

Analysis Calcd. for $C_{14}H_{20}N_4S$: C, 60.84; H, 7.29; N, 20.27; S, 11.60. Found C, 60.76; H, 7.19; N, 20.16; S, 11.73.

EXAMPLE 3

2-Acetylpyridine 4-(2-diethylaminoethyl)-3-thiosemicarbazone dihydrobromide (Procedure A)

By the application of the procedure of R. S. McElhinney [*J. Chem. Soc. (c),* 950 (1966)], 2-diethylaminoethyl isothiocyanate, (bp 54°-55° C. /1.5 mm Hg), was prepared in 20% yield.

Analysis Calcd. for $C_7H_{14}N_2S$: C, 53.12; H, 8.92; N, 17.70; S, 20.26. Found: C, 52.97; H, 8.76; N, 18.01; S, 20.47.

A solution of 1 g (0.063 mol) of 2-diethylaminoethyl isothiocyanate in 5 mL of MeCN was treated with 0.3 g (0.063 mol) of 85% hydrazine hydrate. The solution was heated at reflux for 10 min and the solvent was removed under reduced pressure. The residue was then recrystallized from $C_6H_6$ affording 750 mg (63%) of white needles of 4-(2-diethylaminoethyl)-3-thiosemicarbazide, mp 83°–83.5° C.

Analysis Calcd. for $C_7H_{18}N_4S$: C, 44.18; H, 9.53; N, 29.44; S, 16.85. Found: C, 44.19; H, 9.96; N, 29.56; S, 16.60.

A solution of 605 mg (5 mmol) of 2-acetylpyridine in 10 mL of MeCN was treated with 950 mg (5 mmol) of 4-(2-diethylaminoethyl)-3-thiosemicarbazide and the solution was heated at reflux for 10 hr. The pH of the solution was adjusted to 6 with conc HBr and diluted with 15 mL of $Et_2O$. An oil which separated from solution soon solidified. Crystallization of this product from MeOH-MeCN afforded 1.42 g (64%) of yellow crystals of 2-acetylpyridine 4-diethylaminoethyl)-3-thiosemicarbazone dihydrobromide, mp 231° C. dec.

Analysis Calcd. for $C_{14}H_{23}N_5S \cdot 2HBr$: C, 36.93; H, 5.54; N, 15.38; S, 7.04. Found: C, 36.99; H, 5.52; N, 15.30; S, 7.07.

EXAMPLE 4

2-Acetylpyridine 4-(3-fluorophenyl)-3-thiosemicarbazone (Procedure A)

2-Acetylpyridine (2.0 g, 0.0165 mol) in 70 mL of EtOH and 2.78 g (0.015 mol) 4-(3-fluorophenyl)-3-thiosemicarbazide (mp 152°–155° C.) were heated at reflux temperature for 4 hr. The solution was refrigerated overnight and the product was collected. Recrystallization from MeCN afforded 1.1 g (25%) of 2-acetylpyridine 4-(3-fluorophenyl)-3-thiosemicarbazone, mp 159°–160° C.

Analysis Calcd. for $C_{14}H_{13}FN_4S$: C, 58.32; H, 4.54; N, 19.43; S, 11.12. Found: C, 57.87; H, 4.70; N, 19.41; S, 11.08.

EXAMPLE 5

2-Acetylpyridine 4,4-diisobutyl-3thiosemicarbazone (Procedure B)

A solution of 10 g (0.044 mol) of methyl 3-[1-(2-pyridyl)ethylidene]hydrazinecarbodithioate in 25 mL of MeOH was treated with 7.5 g (0.058 mol) of diisobutylamine and heated at reflux for 6 hr. The solution was chilled and the crystals which formed were collected. Recrystallization from 130 mL of heptane afforded 8.6 g (64%) of yellow needles of 2-acetylpyridine 4,4-diisobutyl-3-thiosemicarbazone, mp 96° C.

Analysis Calcd. for $C_{16}H_{26}N_4S$: C, 62.71; H, 8.55; N, 18.28; S, 10.46. Found: C, 63.27; H, 8.50; N, 18.14; S, 10.21.

EXAMPLE 6

Azacycloheptane-1-thiocarboxylic acid 2-[1-(2-pyridyl)ethylidene]hydrazide (Procedure B)

A solution of 5.0 g (0.022 mol) of methyl 3-[1-(2-pyridyl)ethylidene]hydrazinecarbodithioate in 15 mL of MeOH was treated with 2.2 g (0.022 mol) of hexamethyleneimine and heated at reflux for 5 hr. The solution was chilled, scratched and the product which separated was collected. Recrystallization from 150 mL of MeOH afforded 3.4 g (56%) of yellow needles of azacycloheptane-1-thiocarboxylic acid 2-[1-(2-pyridyl)ethylidene]hydrazide, mp 165° C.

Analysis Calcd. for $C_{14}H_{20}N_4S$: C, 60.84; H, 7.29; N, 20.27; S, 11.60. Found: C, 60.91; H, 7.20; N, 20.30; S, 11.89.

EXAMPLE 7

3-Azabicyclo[3.3.2]heptane-3-thiocarboxylic acid 2-[1-(2-pyridyl)ethylidene]hydrazide (Procedure B)

A solution of 3.8 (0.018 mol) of methyl 3-[1-(2-pryridyl)ethylidene]hydrazinecarbodithioate and 2.1 g (0.017 mol) of 3-azabicyclo[3.2.2]nonane was heated at reflux for 5 hr. The solution was cooled, and the product which crystallized was collected. Recrystallization from 160 mL of MeOH afforded 3.34 g (65%) of yellow needles of 3-azabicyclo[3.2.2]nonane-3-thiocarboxylic acid 2-[1-(2-pyridyl)ethylidene]hydrazide, mp 156° C.

Analysis Calcd. for $C_{16}H_{22}N_4S$: C, 63.54; H, 7.33; N, 18.53; S, 10.60. Found: C, 63.51; H, 7.25; N, 18.55; S, 10.67.

EXAMPLE 8

2-Acetylpyridine 4-cyclohxyl-4-methyl-3-thiosemicarbazone (Procedure B)

A solution of 10 g (0.044 mol) of methyl 3-[1-(2-pyridyl)ethylidene]hydrazinecarbodithioate in 25 mL of MeOH was treated with 7.5 g (0.066 mol) of N-methylcyclohexylamine and the solution heated at reflux for 8 hr. The solution was cooled overnight and the procduct which crystallized was collected. Recrystallization from cyclohexane afforded 9.3 g (72%) of 2-acetylpyridine 4-cyclohexyl-4-methyl-3-thiosemicarbazone, mp 96° C.

Analysis Calcd. for $C_{15}H_{22}N_4S$: C, 62.03; H, 7.64; N, 19.29; S, 11.04. Found: C, 62.07; H, 7.74; N, 19.23; S, 11.14

EXAMPLE 9

2-Acetylpyridine 4-(2-methylbenzyl)-3-thiosemicarbazone (Procedure B)

Methyl 3-[1-(2-pyridyl)ethylidene]hydrazinecarbodithioate (4.51 g, 0.02 mol) and 3.64 g (0.03 mol) 2-methylbenzylamine in 25 mL of methanol were heated under reflux for 36 hr following by overnight refrigeration. The solid material which separated from solution was collected by filtration and recrystallized 3 times from ethanol to afford 2.85 g (48%) of white crystalline 2-acetylpyridine 4-(2-methylbenzyl)-3-thiosemicarbazone having a melting point of 152°–154° C.

Analysis Calcd. for $C_{16}H_{18}N_4S$: C, 64.40; H, 6.08; N, 18.78; S, 10.74. Found: C, 64.17; H, 6.23; N, 19.14; S, 10.64.

EXAMPLE 10

4-(2-Pyridyl)-1-piperazinethiocarboxylic acid 2-[1-(2-pyridyl)ethylidene]hydrazide (Procedure B)

Methyl 3-[1-(2-pryridyl)ethylidene]hydrazinecarbodithioate (3.60 g, 0.016 mol) in 40 mL of EtOH was combined with 3.60 g (0.02 mol) of 1-(2-pyridyl)piperazine. The solution was heated at reflux for 18 hr, cooled and the yellow product which separated was collected. Recrystallization from MeCN afforded 3.45 g (60%) of 4-(2-pyridyl)-1-piperazinethiocarboxylic acid 2-[1-(2-pyridyl)ethylidene]hydrazide, mp 187°–188° C. dec.

Analysis Calcd. for $C_{17}H_{20}N_6S$: C, 59.98; H; 5.92; N, 24.69; S, 9.42. Found: C, 60.65; H, 5.90; N, 24.61; S, 9.41.

EXAMPLE 11

2-Acetylpyridine 4-(2-pyridyl)-3-thiosemicarbazone (Procedure A)

4-(2-Pyridyl)-3-thiosemicarbazide (1.68 g, 0.01 mol) in 125 mL of EtOH and 7.5 mL of glacial acetic acid was treated with 1.21 g (0.01 mol) of 2-acetlypyridine. The solution was heated at reflux for 3 hr, cooled and the product collected. Recrystallization from MeCN afforded 1.8 g (66%) of 2-acetylpyridine 4-(2-pyridyl)-3-thiosemicarbazone, mp 185°–187° C. dec.

Analysis Calcd. for $C_{13}H_{13}N_5S$: C, 57.54; H, 4.83; N, 25.81; S, 11.82. Found: C, 57.03; H, 5.08; N, 25.96; S, 12.17.

EXAMPLE 12

2-Acetylpyridine 4-(1-adamantyl)-3-thiosemicarbazone (Procedure A)

A solution of 1.5 g (0.03 mol) of hydrazine hydrate in 50 mL of EtOH was treated with 3.86 g (0.02 mol) of 1-adamantyl isothiocyanate, and stirred for 1 hr at room temp. The product was collected and washed 2 times with EtOH, affording 4.33 g (96%) of 4-(1-adamantyl)-3-thiosemicarbazide, mp 206°–207° C. dec. This thiosemicarbazide is disclosed in *Chemical Abstracts*, 70:11223 (1969); and in U.S. Pat. No. 3,406,180.

2-Acetylpyridine (2.65 g, 0.022 mol) in 50 mL of EtOH and 2 mol of glacial acetic acid was combined with 4.33 g (0.0195 mol) of 4-(1-adamantyl)-3-thiosemicarbazide, and the solution was heated at reflux for 24 hr. The solution was cooled and the product was collected. Recrystallization from MeCN afford 3.63 g (50%) of 2-acetylpyridine 4-(1-adamatyl)-3-thiosemicarbazone, mp 172°–173° C. dec.

Analysis Calcd. for $C_{18}H_{24}N_4S$: C, 65.82; H, 7.36; N, 17.06; S, 9.76. Found: C, 66.04; H, 7.22; N, 16.88; S, 9.71.

EXAMPLE 13

2-Acetylpyridine 4,4-dimethyl-3-thiosemicarbazone (Procedure A)

To a solution of 2.39 g (0.02 mol) of 4,4-dimethyl-3-thiosemicarbazide in 75 mL of EtOH was added 2.54 g (0.021 mol) of 2-acetylpyridine. After heating at reflux for 8 hr, the solution was cooled and the product was collected. Recrystallization from MeOH afforded 1.2 g (26%) of 2-acetylpyridine 4,4-dimethyl-3-thiosemicarbazone, mp 149°–150° C. dec.

Analysis Calcd. for $C_{10}H_{14}N_4S$: C, 54.03; H, 6.35; N, 25.20; S, 14.42. Found: C, 53.83; H, 6.74; N, 25.25; S, 14.72.

EXAMPLE 14

2-Acetylpyridine 4,4-dimethyl-3-thiosemicarbazone (Procedure B)

Methyl 3-[1-(2-pyridyl)ethylidene]hydrazinecarbodithioate (9.02 g, 0.04 mol) in 30 mL of EtOH was combined with 5.2 g, (0.08 mol) of dimethylamine (40% aqueous solution). The resulting solution was heated at reflux for 24 hr and the excess dimethylamine was removed under water-pump aspiration for 15 minutes. The solution was filtered and cooled to give 7.3 g (82%) of bright yellow crystals of 2-acetylpyridine 4,4-dimethyl-3-thiosemicarbazone, mp 155°–156° whose infrared spectrum was identical to that of the product made by the method described in Example 13.

EXAMPLE 15

1-Azacycloheptane-1-thiocarboxylic acid 2-[1-(2-pyridyl)propylidene]hydrazide (Procedure B)

Methyl 3-[1-(2-pyridyl)propylidene]hydrazinecarbodithioate (4.77 g, 0.02 mol) and 3.4 mL (3.0 g, 0.03 mol) hexamethyleneimine in 25 mL of MeOH were heated under reflux for 48 hr followed by overnight refrigeration. The solid material which separated from solution was collected by filtration and recrystallized from MeOH to afford 3.65 g (63%) of yellow crystalline 1-azacycloheptane-1-thiocarboxylic acid 2-[1-(2-pyridyl)propylidene]hydrazide, mp 117°–119° C.

Analysis Calcd for $C_{15}H_{22}N_4S$: C, 62.03; H, 7.64; N, 19.29; S, 11.04. Found: C, 62.14; H, 7.64; N, 19.14; S, 11.16.

UTILITY

The compounds of this invention possess medicinal activity. More specifically, evidence indicates that all the compounds and their pharmaceutically acceptable acid addition salts demonstrate activity against *Neisseria gonorrhoeae*, including penicillin-resistant strains, and are therefore useful in the treatment of gonorrhea. In addition, many compounds and salts are useful either in the treatment of malaria (active against *Plasmodium berghei*) or bacterial infection (active against *Staphylococcus aureus*; Group D Enterococcus; and *Neisseria meningitidis*.

Several tests have been made to determine the activity of the compounds of this invention. In order to guide one of ordinary skill in the practice of the invention, these tests are described below, as well as results obtained in each test with a representative sampling of compounds. Compounds are coded by letter as follows:

A. 2-Acetylpyridine 4-allyl-3-thiosemicarbazone
B. 2-Methylpiperidine-1-thiocarboxylic acid 2-[1-(2-pyridyl)ethylidene]hydrazide
C. 2-Acetylpyridine 4-(2-picolyl)-3-thiosemicarbazone
D. 2-Acetylpyridine 4-cyclohexyl-3-thiosemicarbazone
G. 2-Acetylpyridine 4-(1,1,3,3-tetramethylbutyl)-3-thiosemicarbazone
H. 1-Azacycloheptane-1-thiocarboxylic acid 2-[1-(2-pyridyl)ethylidene]hydrazide
I. 1,4-Diaza-4-carboethoxycyclohexane-1-thiocarboxylic acid 2-[1-(2-pyridyl)ethylidene]hydrazide K. 1,4-Diaza-4-phenylcyclohexane-1-thiocarboxylic acid 2-[1-(2-pyridyl)ethylidene]hydrazide L. 3-Azabicyclo[3.2.2]nonane-3-thiocarboxylic acid 2-[1-(2-pyridyl)ethylidene]hydrazide N. 2-Acetylpyridine 4-(2-methylbenzyl)-3-thiosemicarbazone O. 2-Acetylpyridine 4,4-diisobutyl-3-thiosemicarbazone R. 2-Acetylpyridine 4,4-dimethyl-3-thiosemicarbazone S. 2Acetylpyridine 4-(1-adamantyl)-3-thiosemicarbazone V. 1,4-Diaza-4-(2-pyridyl)cyclohexane-1-thiocarboxylic acid 2-[1-(2-pyridyl)-ethylidene]hydrazide W. 1,4-Diaza-4-(2-pyridyl)cyclohexane-1-thiocarboxylic acid 2-[1-(2pyridyl-ethylidene]hydrazide dihydrochloride Z. 1-Azacyclotridecane-1-thiocarboxylic acid 2-[1(2-pyridyl)ethylidene]-hydrazide AA. 2-Ethylpiperidine-1-thiocarboxylic acid 2-[1-(2-pyridyl)ethylidene]-hydrazide FF. Azetidine-1-thiocarboxylic acid 2-[1-(2-pyridyl)ethylidene]hydrazide GG. Piperidine-1-thiocarboxylic acid 2-[1-(2-pyridyl)ethylidene]hydrazide HH. 1-Azacyclopentane-1-thiocarboxylic acid 2-[1-(2pyridyl)ethylidene]hydrazide JJ. 2-Propionylpyridine 4,4-dimethyl-3-thiosemicarbazone

TEST 1

Compounds were tested against five isolates of *Staphylococcus aureus* and five isolates of Group D Enterococcus. The bacteria used were isolated from patients at the Walter Reed Army Medical Center, Washington, D. C. The test procedure used was the macro broth dilution method in duplicate as outlined by J. C. Sherris on pages 414-415 in "Manual of Clinical Microbiology," 2nd ed., E. Lennette, E. H. Spaulding, and J. P. Truant, Ed. (American Society for Microbiology, Washington, D.C., 1974). Each compound was dissolved in DMSO (12.8 mg/mL) and then diluted with Mueller-Hinton broth to obtain the desired dilutions. Tubes containing the highest quantities of DMSO with no compound present were run as controls. The results were read after 24 hours and are summarized in Tables 1 and 2 below. DMSO controls showed no inhibition of bacterial growth.

TABLE 1

| Compound | Minimum Inhibitory Concentration (μg/mL) Staphylococcus aureus isolates | | | | |
|---|---|---|---|---|---|
| | I | II | III | IV | V |
| B | 1 | 1 | 1 | 1 | 1 |
| D | 0.5 | 0.5 | 0.5 | 1 | 0.5 |
| L | 1 | 1 | 1 | 1 | 1 |
| N | 2 | 2 | 2 | 2 | 1 |
| O | 0.5 | — | 1 | 0.5 | 0.5 |
| S | 2 | 2 | 4 | 2 | 1 |

TABLE 2

| Compound | Minimum Inhibitory Concentration (μg/mL) Group D Enterococcus isolates | | | | |
|---|---|---|---|---|---|
| | I | II | III | IV | V |
| D | 4 | 8 | 8 | >8 | 8 |
| G | 8 | 4 | 4 | 4 | 4 |
| H | 4 | 4 | 4 | 4 | 4 |
| L | 2 | 2 | 2 | 2 | 2 |
| O | 2 | 2 | 2 | 4 | 2 |

TABLE 2-continued

| Compound | Minimum Inhibitory Concentration (μg/mL) Group D Enterococcus isolates | | | | |
|---|---|---|---|---|---|
| | I | II | III | IV | V |
| S | 2 | 1 | 2 | 2 | 2 |

TEST 2

Compounds were tested against five isolates of *Neisseria meningitidis*. The bacterial isolates were provided by the Department of Bacterial Diseases of the Walter Reed Army Institute of Research. The test procedure used was the macro broth dilution method in duplicate outlined by J. C. Sherris on pages 414-415 (loc. cit.). The test compounds and control were prepared as in Test 1 above. Ampicillin and penicillin standards were initially diluted as described by J. C. Sherris on pages 411-412 (loc. cit.) followed by dilution with Mueller-Hinton broth. The tubes were incubated at 37° C. under 5-10% carbon dioxide. The test results were read after 24 hours and are summarized in Table 3 below. DMSO controls showed no inhibition of bacterial growth.

TABLE 3

| Compound | Minimum Inhibitory Concentration (μg/mL) Neisseria meningitidis isolates | | | | |
|---|---|---|---|---|---|
| | 7957 | 7990 | 8005 | 8006 | 8011 |
| B | 0.062 | 0.062 | 0.125 | 0.062 | 0.5 |
| H | 0.031 | 0.062 | 0.062 | 0.125 | 0.062 |
| K | 0.062 | 0.062 | 1.0 | 0.062 | 0.125 |
| L | 0.031 | 0.062 | <0.031 | 0.062 | 0.125 |
| O | 0.062 | 0.125 | 0.5 | 0.062 | 0.5 |
| R | 0.062 | 0.125 | 0.062 | 0.062 | 0.125 |
| V | 0.062 | 0.125 | 0.125 | 0.125 | 0.25 |
| Penicillin | 0.031 | 0.031 | — | 0.031 | 0.031 |
| Ampicillin | 0.008 | 0.008 | 0.008 | 0.016 | 0.016 |

TEST 3

Compounds were tested against six *Neisseria gonorrhoeae* isolates. The bacteria used were provided by the Department of Bacterial Diseases of the Walter Reed Army Institute of Research. The test procedure used was the agar dilution method in duplicate as outlined by J. C. Sherris on pages 411-412 (loc. cit.). GC Medium (Difco) with a 2% defined supplement added as described by D. S. Kellogg et al. [*J. Bact.* 85:1274-1279 (1963)] was used as the media. The compounds were dissolved in DMSO (1.0 mg/ml), diluted with GC broth (GC medium without agar) to the appropriate concentration, and added to the GC Medium at 55°-56° C. The latter was then poured and allowed to solidify. A penicillin standard was also prepared with initial dilutions as described by J. C. Sherris followed by dilutions with GC broth and addition to the GC Medium at 55°-56° C. as above. The inoculum was 1:200 GC broth dilution of a suspension of colony isolates after the suspension was adjusted visually to the turbidity standard described by J. M. Matsen and A. L. Barr on page 422 in "Manual of Clinical Microbiology," 2nd ed., E. Lennette, E. H. Spaulding, and J. P. Truant, Ed. (American Society for Microbiology, Washington, D.C., 1974). The plates were inoculated with a replicator and incubated at 37° C. under 5-10% carbon dioxide. The results were read after 24 hours and are summarized in Table 4 below. DMSO controls showed no inhibition.

TABLE 4

| | Minimum Inhibitory Concentration (μg/mL) | | | | | |
|---|---|---|---|---|---|---|
| | Neisseria gonorrhoeae isolates | | | | | |
| Compound | 135 | 161 | 278 | 455 | 456 | 602 |
| H | 0.031 | 0.016 | 0.031 | 0.031 | 0.016 | 0.031 |
| K | 0.031 | <0.008 | 0.031 | 0.031 | 0.016 | 0.031 |
| L | 0.031 | 0.016 | 0.031 | 0.031 | 0.031 | 0.031 |
| R | 0.004 | 0.004 | 0.008 | 0.008 | 0.008 | 0.008 |
| V | 0.016 | <0.008 | 0.031 | 0.016 | 0.016 | 0.016 |
| GG | 0.008 | 0.004 | 0.008 | 0.008 | 0.008 | 0.008 |
| HH | 0.008 | 0.004 | 0.008 | 0.008 | 0.008 | 0.008 |
| JJ | 0.016 | 0.004 | 0.016 | 0.008 | 0.008 | 0.008 |
| Penicillin | 0.25 | 0.125 | <0.062 | 0.125 | >16 | >16 |

TEST 4

Compounds were tested against four strains of *Mycobacterium smegmatis*. The test procedure used was as mentioned by N. E. Morrison [Int. J. of Leprosy 39:34–43 (1971)]. The results are summarized in Table 5 below. The strain numbers refer to *Mycobacterium smegmatis* ATCC 607, a DDS-resistant daughter strain, a Rifampin-resistant daughter strain, and a Clofazimine-resistant daughter strain, respectively.

TABLE 5

| | Minimum Inhibitory Concentration (μg/mL) | | | |
|---|---|---|---|---|
| | Mycobacterium smegmatis strains | | | |
| Compound | I | II | III | IV |
| A | <1 | <1 | <1 | <1 |
| R | 2 | 3 | 2 | 2 |
| W | 6 | 10 | 5 | 6 |
| Y | 5 | 4 | 10 | 10 |
| AA | 5 | 10 | 10 | 10 |
| FF | 2 | 2 | <1 | <1 |
| HH | 2 | 3 | 2 | 4 |
| DDS | 2 | 400 | — | — |
| Ritampin | 1 | — | 250 | — |
| Clofazimine | 1.5 | — | — | 20 |

Test 5

Compounds were tested against *Plasmodium berghei* KBG 173 malaria in mice following the procedure described by T. S. Osdene, P. B. Russel, and L. Rane [*J. Med. Chem.* 10:431–434 (1967)]. Five mice were tested at each dosage level. Mice surviving 60 days are considered cured. Toxicity is defined as a decrease in the mean survival time of the treated mice as compared to the control group. Activity is defined as a 100% increase in the mean survival time of the treated mice compared to the control group. The ED$_{50}$ is a computed estimate of the dose required to cure 50% of the mice. The results are summarized in Table 6 below.

TABLE 6

| | In vivo Antimalarial Activity | | | | | | | |
|---|---|---|---|---|---|---|---|---|
| | Dosage Level (mg/kg) | | | | | | | |
| Compound | 10 | 20 | 40 | 80 | 160 | 320 | 640 | ED$_{50}$ (mg/kg) |
| B | — | — | C(1/5) | C(4/5) | Active | Toxic | Toxic | 57 |
| H | — | — | Active | C(4/5) | C(3/5) | C(2/5) | C(2/5) | 72 |
| I | Active | Active | C(2/5) | — | Toxic | — | Toxic | — |
| L | — | C(1/5) | C(2/5) | C(3/5) | C(4/5) | — | — | 59 |
| V | — | — | C(1/5) | C(5/5) | C(2/5) | — | Toxic | 45 |
| AA | — | — | — | C(1/5) | C(4/5) | C(2/5) | — | 113 |

C = Cure

TEST 6

Compounds were tested against six strains of *Mycobacterium intracellulare*. The test procedure used was a broth dilution technique described by A. L. Barry on pages 92–104 in "The Antimicrobic Susceptibility Test: Principles and Practices," (Lea & Febiger, Philadelphia, PA, 1976). The compounds were dissolved in and diluted with DMSO and added to tubes of 7H9 broth. Tubes containing the same quantities of DMSO and broth but no compound were run as controls. All tubes were incubated at 35° C. The results are summarized in Table 7 below. DMSO controls showed no inhibition of bacterial growth.

TABLE 7

| | Minimum Inhibitory Concentration (μg/mL) | | | | | |
|---|---|---|---|---|---|---|
| | Mycobacterium intracellulare strains | | | | | |
| Compound | I | II | III | IV | V | VI |
| H | 1 | 1 | 1 | 1 | 1 | 1 |
| L | 10 | 1 | 1 | 0.1 | 0.1 | 0.1 |
| S | 10 | 1 | 1 | 10 | 10 | 10 |
| Z | 10 | 1 | 1 | 10 | 10 | 10 |
| AA | 10 | 1 | 1 | 1 | 10 | 10 |

We claim:

1. A compound of the formula

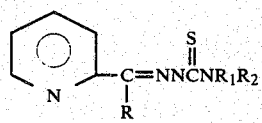

or a pharmaceutically-acceptable acid addition salt thereof wherein R is methyl or ethyl; and R$_1$ and R$_2$ are taken together with the nitrogen atom to which they are attached to form a heterocyclic ring selected from the group consisting of homopiperazinyl; homopiperazinyl substituted with alkyl; piperazinyl; or piperazinyl substituted with alkyl, dialkyl, phenyl, COO alkyl, trifluoromethylphenyl, halophenyl, benzyl, or pyridyl; or

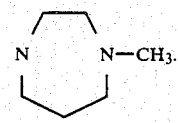

2. A compound or salt of claim 1 wherein R is methyl.
3. A compound or salt of claim 1 wherein R is ethyl.
4. A compound or salt of claim 2 wherein NR$_1$R$_2$ is

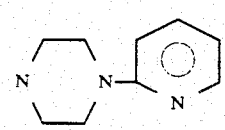
5. A compound or salt of claim 3 wherein $NR_1R_2$ is
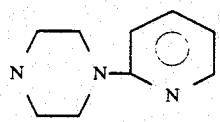
6. A compound or salt of claim 2 wherein $NR_1R_2$ is
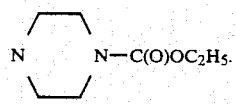
7. A compound or salt of claim 3 wherein $NR_1R_2$ is
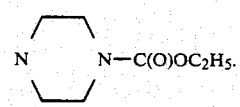
8. A compound or salt of claim 2 wherein $NR_1R_2$ is
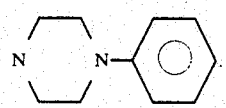
9. A compound or salt of claim 3 wherein $NR_1R_2$ is
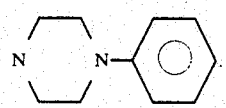
10. A compound or salt of claim 2 wherein $NR_1R_2$ is
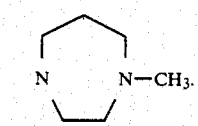
11. A compound or salt of claim 3 wherein $NR_1R_2$ is
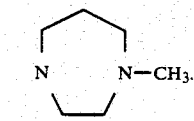
* * * * *